US00PP16624P2

(12) United States Plant Patent
Banning

(10) Patent No.: US PP16,624 P2
(45) Date of Patent: Jun. 6, 2006

(54) APPLE TREE NAMED 'BANNING RED FUJI'

(50) Latin Name: *Malus×pumila*
Varietal Denomination: Banning Red Fuji

(75) Inventor: Bob L. Banning, East Wenatchee, WA (US)

(73) Assignee: Banning Orchards & Nursery, East Wenatchee, WA (US)

( * ) Notice: Subject to any disclaimer, the term of this patent is extended or adjusted under 35 U.S.C. 154(b) by 51 days.

(21) Appl. No.: 11/009,105

(22) Filed: Dec. 10, 2004

(51) Int. Cl.
*A01H 5/00* (2006.01)

(52) U.S. Cl. ..... Plt./168

(58) Field of Classification Search ..... Plt./168
See application file for complete search history.

*Primary Examiner*—Anne Marie Grunberg
*Assistant Examiner*—June Hwu
(74) *Attorney, Agent, or Firm*—Klarquist Sparkman, LLP

(57) ABSTRACT

A new 'Fuji' apple variety distinguished by fruit with dark red striping over a lighter red ground color and with large average fruit size for a 'Fuji' apple tree.

5 Drawing Sheets

Latin name of the genus and species of the plant claimed: *Malus×pumila,* Mill.

Variety denomination: 'Banning Red Fuji'.

BACKGROUND OF THE INVENTION

The present invention relates to a new and distinct variety of apple tree (*Malus pumila,* Mill.) discovered in East Wenatchee, Wash. growing in a cultivated block of 'Desert Rose Fuji' (not patented). 'Desert Rose Fuji' is a sport of 'BC 2 Fuji' (not patented) apple trees. These 'Desert Rose Fuji' trees were growing on 'M 26' rootstock (not patented) planted in 1994. In the late summer (August) of 1999, I noticed on one of the 'Desert Rose Fuji' trees a one-inch diameter branch with four apples that had fruit with distinctly more striping and color than the fruit on the rest of the tree. This branch mutation is the origin of my new variety.

BRIEF SUMMARY OF THE INVENTION

The 'Banning Red Fuji' variety is distinguished from other apple varieties due to the following unique combination of characteristics: fruit with dark red striping over lighter red ground color and an increase in average fruit size for a 'Fuji' apple tree. In addition, the fruit has stems that are longer on average than stems of 'Desert Rose Fuji' trees.

Asexual reproduction of this new variety shows that the foregoing characteristics come true to form, are firmly fixed, and are established and transmitted through succeeding propagations. In 1999, buds from the original 'Banning Red Fuji' mutated branch mutation were obtained and used to bud limbs of four adjacent 'Desert Rose Fuji' trees growing on 'M 26' (not patented) root stock. These first generation trees were top budded with the budded 'Banning Red Fuji' branches being left on the top worked trees and the 'Desert Rose Fuji' branches being removed after the buds became established branches. These first generation trees produced 'Banning Red Fuji' fruit in 2001 that were identical to fruit on the original 'Banning Red Fuji' mutation branch. Upon confirming the stable nature of this mutation, buds from 'Banning Red Fuji' branches on these first generation trees were used to graft five 'Imperial Gala' (not patented) trees in an orchard in Quincy, Wash. These five second generation trees were top worked to leave the 'Banning Red Fuji' branches after the grafts were established. These five second generation trees were also growing on M26 rootstock. The second generation trees, grafted in 2001, have produced apples that appear identical to the apples from the original 'Banning Red Fuji' mutated branch and to apples from the first generation trees. In 2002, 300 'Banning Red Fuji' trees in East Wenatchee were obtained by grafting on 'M 9' (not patented) rootstock. These third generation trees have produced only a few apples, but these apples also appear identical to those from the earlier generations of 'Banning Red Fuji' trees.

Certain characteristics of this variety, such as growth and color, may change with changing environmental conditions, such as photoperiod, temperature, moisture, soil conditions, nutrient availability, or other factors). For example, leaf colors may be brighter green if the trees are grown in soil with greater nitrogen concentrations, and may be more yellow when grown in soil containing lesser amounts of nitrogen. Color descriptions and other terminology are used in accordance with their ordinary dictionary descriptions, unless the context clearly indicates otherwise. Color designations (hue/value/chroma) are made with reference to the Munsell Book of Color, Kollmorgen Instruments Corp., 405 Little Britain Road, New Windsor, N.Y. 12553.

Figure 1:
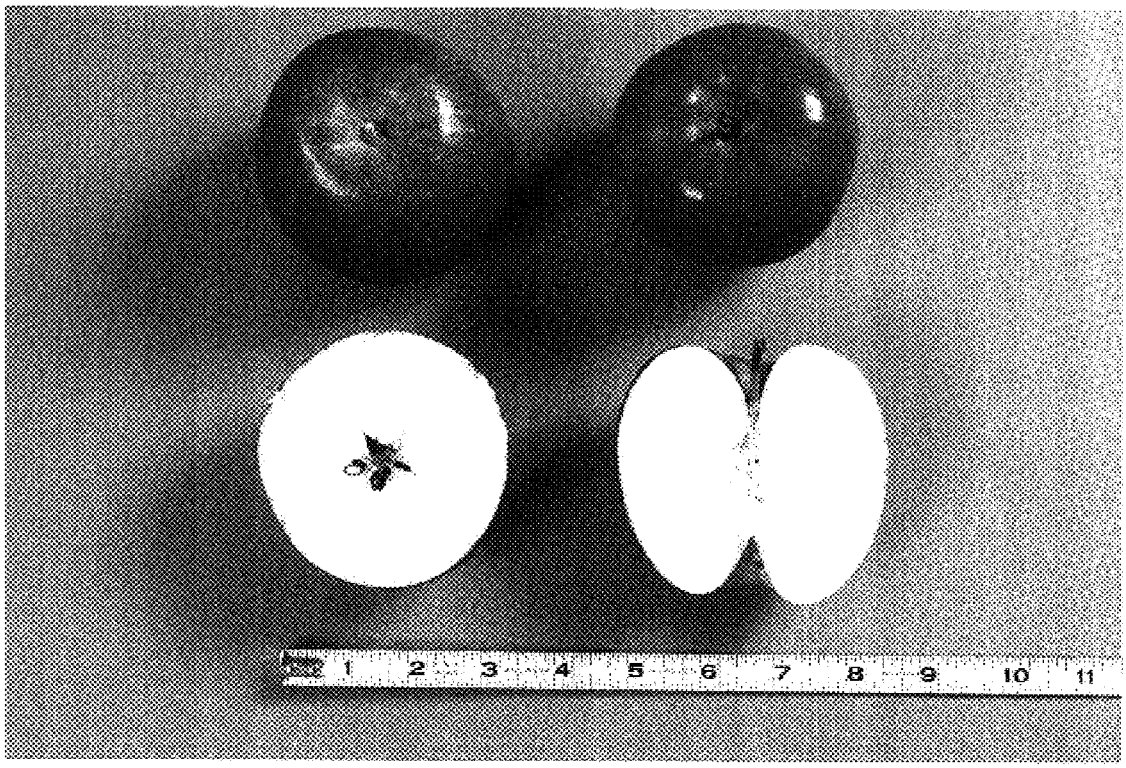
FIG. 1 is a photograph showing various aspects of 'Banning Red Fuji' fruit, showing cavity, basin, and transverse and longitudinal sections.
Figure 2:
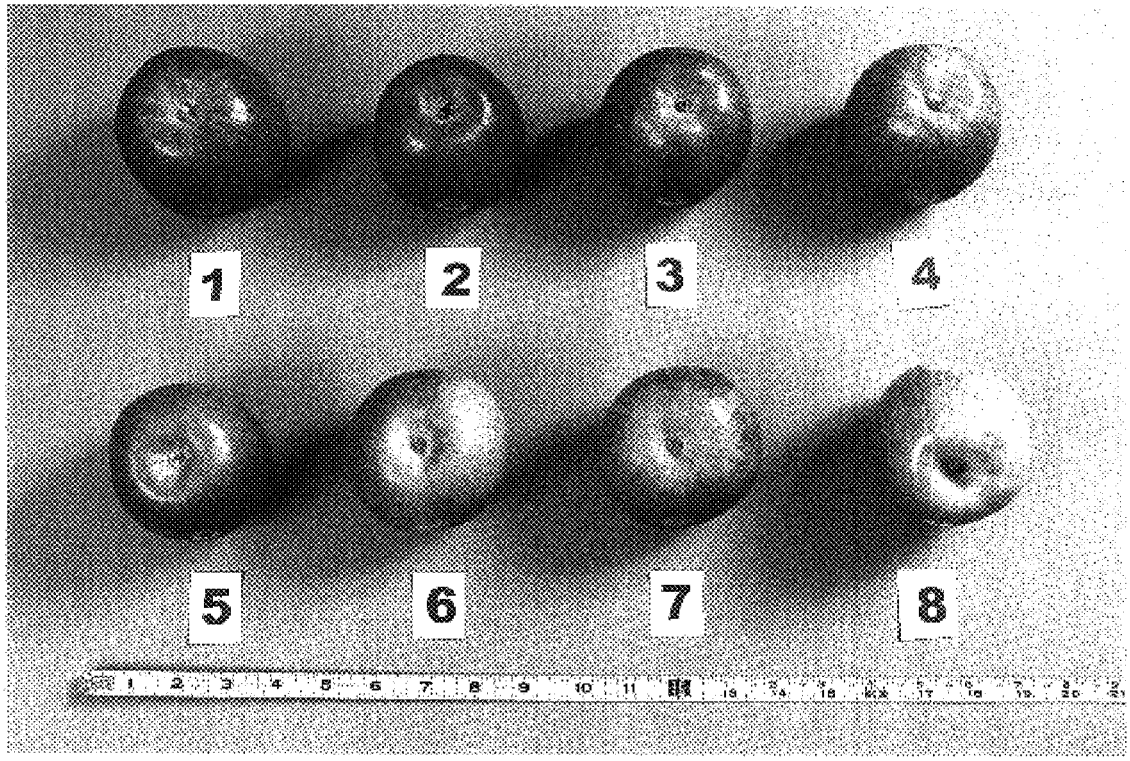
FIG. 2 is a photograph showing the basin end of the following 'Fuji' strains: 1. 'Banning Red Fuji'; 2. 'Desert Rose Fuji' (unpatented); 3. 'Nagafu 12' (unpatented); 4. 'Snyder' (U.S. Plant Pat. No. 12,098); 5. 'Myra' (U.S. Plant Pat. No. 9,645); 6. 'BC 2' (unpatented); 7. 'Nagafu 6' (unpatented); and 8. standard 'Fuji' (unpatented).
Figure 3:
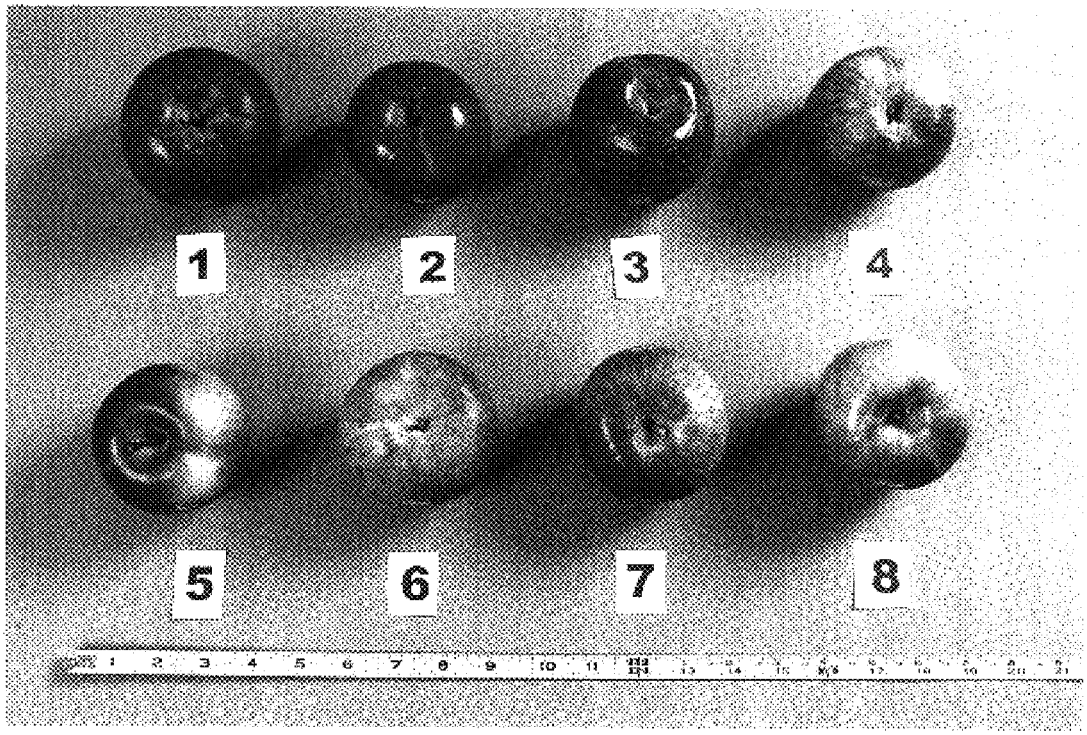
FIG. 3 is a photograph showing the stem ends of the 'Fuji' strains of FIG. 2 with each variety in FIG. 3 having the same number as in FIG. 2.
Figure 4:
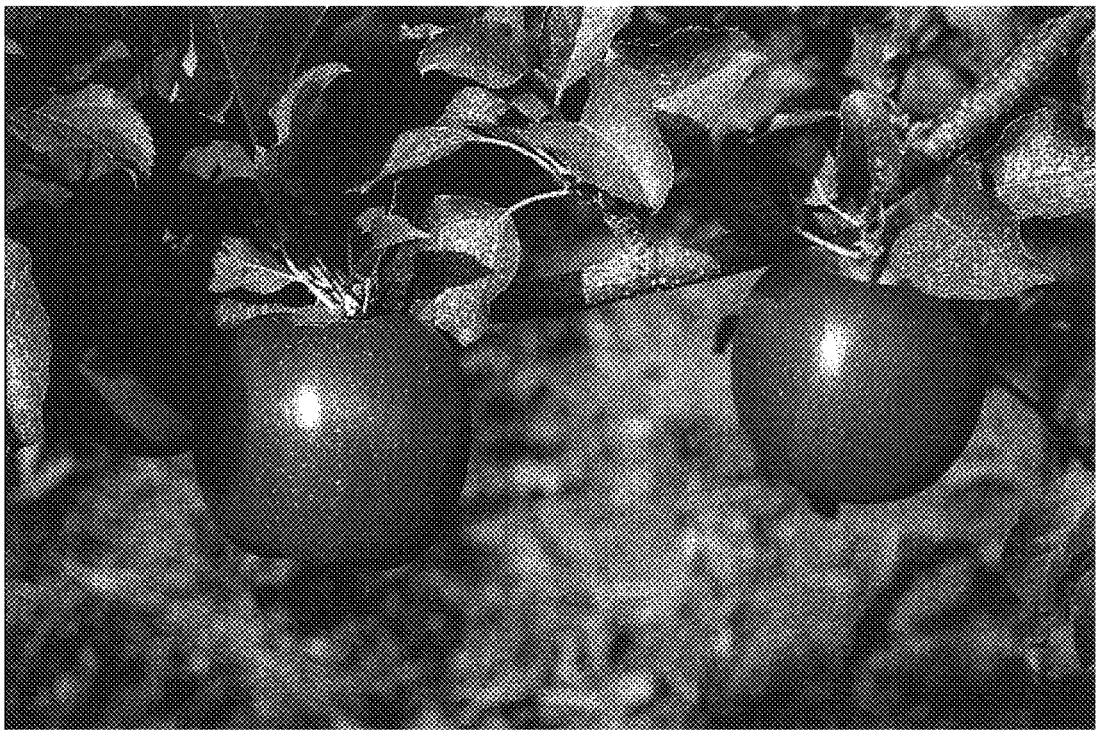
FIG. 4 is a photograph showing the original branch mutation of the 'Banning Red Fuji' variety including leaves and fruit.
Figure 5:
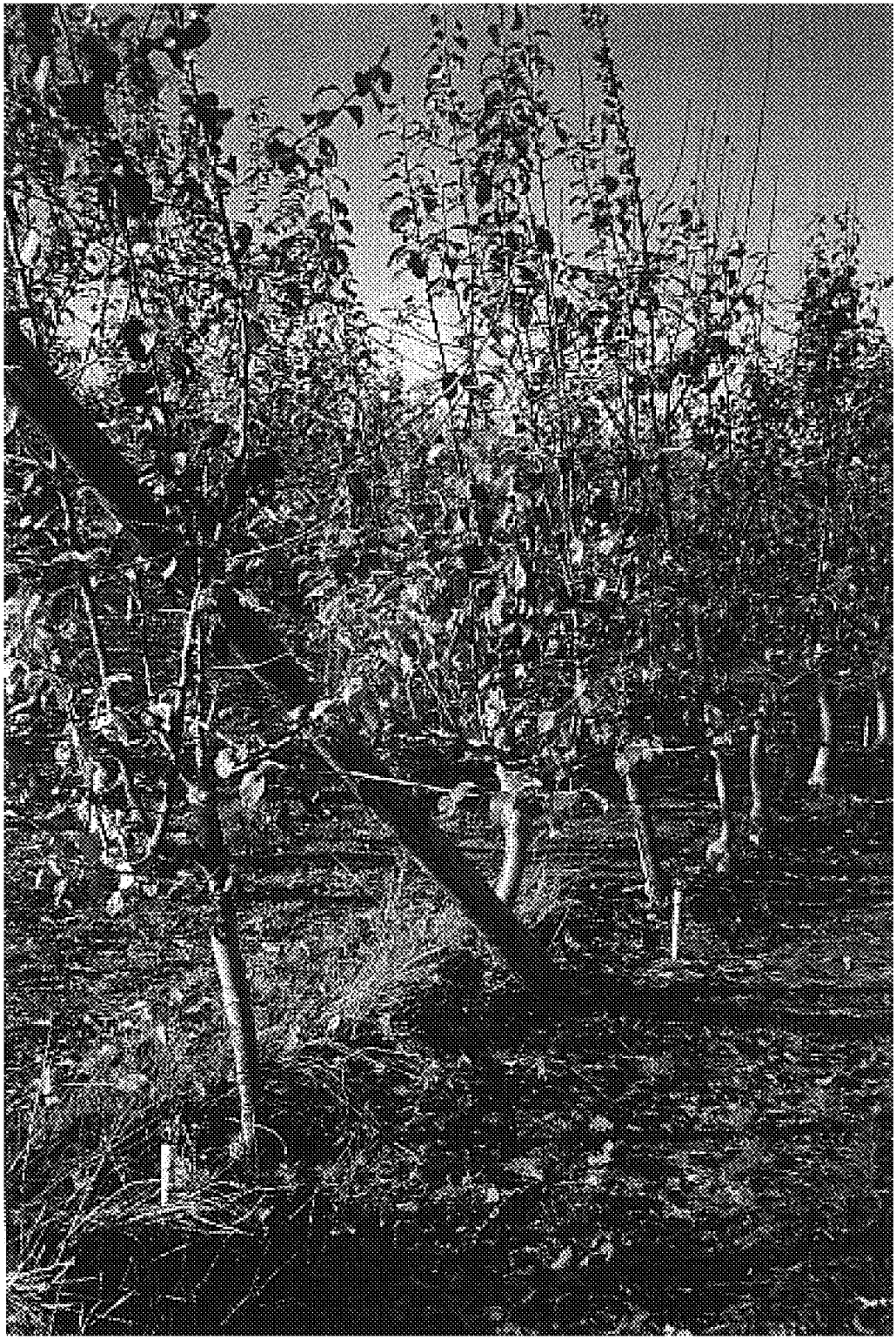
FIG. 5 is a photograph showing a few of the third generation trees growing on M9 rootstock.

The accompanying color photographs show typical specimens of the fruit of this new apple tree variety and depict the color as nearly true as is reasonably possible to make the same in a color illustration of this character. It should be noted that colors may vary, for example due to lighting conditions at the time the photographs are taken. Therefore, color characteristics of this new variety should be determined with reference to the observations described herein, rather than from the photographs alone.

DETAILED DESCRIPTION

The following detailed description of the 'Banning Red Fuji' cultivar apple tree is based on observations of the original 'Banning Red Fuji' mutated branch growing on the 'Desert Rose Fuji' tree in East Wenatchee, Wash. and on observations of grafted 'Banning Red Fuji' trees growing on 'M26' (not patented) root stock.

Scientific name: *Malus×pumila,* Mill. 'Banning Red Fuji'.

Parentage: Limb mutation of 'Desert Rose Fuji' (not patented).

Tree:

*Overall shape.*—Upright-spreading (typical 'Fuji' shape).

*Vigor.*—Medium to high; average seasonal growth in East Wenatchee, Wash., approximately 28 to 48 cm.

*Productivity.*—Annually productive when properly thinned.

*Height and spread.*—'Banning Red Fuji' tree at 5 years from grafting onto 'M26' (not patented) understock growing in Quincy, Wash., was 8 feet tall by 5 feet spread.

Trunk (original mutated branch was found at 2 m height on 'Desert Rose Fuji' tree and was a central, nearly vertical primary branch and therefore is described as a trunk in this description):

*Size.*—2.5 cm diameter at 0.5 m from origin of mutation.

*Trunk bark texture.*—Smooth, with raised lenticels, about 4 per square centimeter; similar to that of standard 'Fuji' (not patented).

*Trunk bark color.*—Tan with slightly orange tint (7.5 YR 4/4).

Trunk caliper of third generation trees growing on M9 rootstock observed in the Fall of 2004 to be 2.25 inches 1 foot from the ground.

Branches:

*Primary branches.*—Upright to spreading, similar to those of standard 'Fuji'.

Two-year-old branches averaged 9 mm in diameter and 89 cm in length.

Branch angle at emergence typically 50 to 70 degrees from the vertical, similar to standard 'Fuji'.

*Branch color.*—One-year shoot bark color ranges from green (2.5 GY 5/4) lower surface to brownish purple (7.5 R ¾) upper surface; two-year-old branch becoming light brown (5 YR 4/4).

*Branch pubescence.*—Mostly glabrous to very fine, colorless pubescence at nodes.

*Branch lenticels.*—Round to elongated, decreasing in density from base of branch to terminal; size 0.5×1.2 mm; light tan (7.5 YR 6/2).

*Internodes.*—Average internode length on one-year-shoot 4.0 cm.

Leaves (observations were of 10 leaves in June 2004.):

*Texture.*—Smooth, with slightly rugose upper surface; similar to that of standard 'Fuji'.

*Sheen.*—Somewhat glossy.

*Length.*—About 7 cm to about 9.0 cm, averaging about 8.2 cm.

*Width.*—About 5.5 to 7.0 cm, averaging about 6.0 cm.

*Petiole.*—About 32 mm in length, 2 mm in diameter. Color of petiole is light green (10 Y 7/4).

*Form.*—Oval, tapering to tip.

*Marginal form.*—Finely serrate to crenate.

*Tip.*—Acute.

*Stipules.*—Present on all leaves of vigorous one-year shoots; variable in length from 7 to 15 mm, in width from 0.5 to 3 mm.

*Leaf color.*—Upwardly disposed surface: dark green (5 GY 4/4). Downwardly disposed surface: medium green (5 GY 6/4). Vein: light green (2.5 GY 8/4).

*Pubescence.*—Very fine, colorless.

Flowers (observations are from sampling of flowers from the original 'Banning Red Fuji' mutated branch.):

*Size.*—Individual flowers are medium size (typically about 45 mm fully open), similar in appearance to standard 'Fuji'.

*Bloom description.*—Flowers generally in clusters of 5 flowers per spur.

*Flower color.*—Bud (popcorn stage): light pink (7.5 RP 7/8), similar to standard 'Fuji'. Fully open flower, upper side pure white, reverse side pure white.

*Petals.*—Oblong, typical petals about 20 mm in length and about 13 mm in width.

*Stamen.*—Arranged in a single row. About 18 stamens, each about 6 mm in length.

*Filament.*—About 6 to 7 mm in length.

*Anthers.*—Light yellow (5 Y 8.5/10).

*Pistil.*—Stigma: round to oblong stigmatal surface. Style: five filaments fused at base, approximately 10 mm in length.

*Sepal.*—Recurved downward, light green (2.5 GY 7/6), with fine, colorless pubescence. Sepals are about 6 mm in length, 3 mm wide at base, recurved to expose persistent stamen.

*Pollen.*—Light yellow (5 Y 8.5/10). Fragrance: medium, fruity, typical of 'Fuji', but not distinctive.

*Time of bloom.*—During the year 2004 at East Wenatchee: first bloom April 25; full bloom May 5, petal fall May 10. (2004 was an exceptionally early bloom year.) Bloom of this variety was not different from that of adjacent 'Desert Rose Fuji' trees.

*Fertility.*—Diploid. Presumed to be identical to that of other 'Fuji' strains.

*Eye (calyx or calyx tube).*—Closed.

*Peduncle.*—About ¾ inch in length.

Fruit (observations from ten samples of typical fruit grown in East Wenatchee, Wash. in September/October 2003.): Maturity when described was mid-harvest period, Oct. 15, 2003 at East Wenatchee, Wash.

*Maturity.*—Identical to that of standard Fuji (not patented).

*Firmness.*—19 to 22 pounds (Taylor-Magress pressure tester).

Soluble solids reading (refractometer) was 14 to 16%.

*Malic acid content* (*titration*).—0.45%.

Starch index (1 to 6 scale) was 3.5.

*Size.*—Large, about 9 to 10 cm (3.6 to 4 inches); box size 56 to 80. Average 72 box size (72 apples per 42 pound box) in comparison to 80 box size (80 apples per 42 pound box) for 'Desert Rose Fuji' apples growing in Wenatchee, Wash. area during one growing season. Average weight 365 grams in our observation of a sampling of typical apples.

*Form.*—Round, symmetric; length/diameter ratio approximately 0.9:1, with no ribbing; distal end smooth, with no lobes.

*Stem cavity.*—Medium width (about 30 mm); medium depth, (about 12 mm); acute.

*Basin cavity.*—Medium (about 35 mm), shallow to medium depth (about 8 to 10 mm).

*Stem.*—Medium length (14 to 22 mm); width 2 mm, with clubbed terminal end; the stems being longer on average than those of 'Desert Rose Fuji' fruit stems; greenish (10 Y 6/6) to reddish brown (2.5 R 54), with very fine colorless pubescence.

*Locules* (*carpels*).—Medium size, 5 in number, closed.

*Skin.*—Texture smooth; naturally glossy but not greasy; not prone to russet; occasional cracking in stem cavity with advanced maturity; skin thin and tender.

*Lenticels.*—Light tan (2.5 Y 8/2); medium density (9 per square cm); small, round, less than 1 mm in diameter.

*General color effect.*—Bright pink-red blush, most apples 80 to 100% blushed.

*Ground color.*—Honey red (5 Y 8/8).

*Over color.*—Deep bright red (5 R 3/10).

*Russet.*—None observed.

*Flesh.*—Color off white (7.5 Y 9/2).

*Texture.*—Crisp and juicy, retaining crispness throughout long storage period.

*Flavor.*—Sweet, typical of standard 'Fuji'.

*Acidity.*—Low for early ripening variety, approximately 0.5% malic acid.

*Aroma.*—None.

*Core.*—Round, small, about 22 mm width by about 30 mm length; number of bundles: ten; core lines sharply defined; core mostly closed, calyx tube short, closed.

*Seed.*—Obovate in shape, usually 2 per cell, brown (10 YR 3/6); length about 7 mm width about 4 mm, with tight adherence to carpel wall.

*Keeping quality.*—Exceptional; fruit remains firm and crisp at room temperature for almost four weeks.

*Storage.*—Up to 8 months in common storage (0 degrees C.); 12 months in controlled atmosphere (CA) storage.

*Usage.*—Primarily for fresh eating (dessert), but acceptable for culinary uses, including sugarless preparations.

*Cold hardiness.*—Not tested, but presumably similar to that of standard 'Fuji', which is considered to be as hardy as its parents, 'Red Delicious' and 'Ralls Janett'.

*Disease resistance.*—Similar to that of standard 'Fuji', susceptible to apple scab, moderately susceptible to powdery mildew and fire blight. This cultivar has been grown only in the area of origination, near Wenatchee, Wash.

TABLE 1

COMPARISON OF FUJI STRAINS

| | Fuji Strain | Patent Status | Type | Percent Red Skin | Percent Size* |
|---|---|---|---|---|---|
| 1. | 'Banning Red' | (This Application) | Intermediate | 100% | 110% |
| 2. | 'Desert Rose' | Not patented | Blush | 100% | 100% |
| 3. | 'Nagafu 12' | Not patented | Intermediate | 80% | 100% |
| 4. | 'Snyder' | U.S. Plant Pat. No. 12098 | Stripe | 70% | 100% |
| 5. | 'Myra' | U.S. Plant Pat. No. 9645 | Blush | 80%+ | 100% |
| 6. | 'BC 2' | Not patented | Intermediate | 55% | 100% |
| 7. | 'Nagafu 6' | Not patented | Stripe | 50% | 100% |
| 8. | Standard | Not patented | Stripe | 30% | 100% |

*As relates to average Fuji size. Intermediate refers to being between a full stripe and a full blush.

I claim:

1. A new and distinct variety of apple tree, substantially as herein shown and described.

* * * * *